(12) United States Patent
Alitalo et al.

(10) Patent No.: US 6,974,816 B2
(45) Date of Patent: Dec. 13, 2005

(54) COMBINATION FOR THE TREATMENT OF ENDOTHELIAL DAMAGE

(75) Inventors: Kari Alitalo, Helsinki (FI); Carl-Henrik Heldin, Uppsala (SE); Olli Leppänen, Uppsala (SE); Arne Östman, Uppsala (SE); Seppo Ylä-Herttuala, Vuirela (FI)

(73) Assignees: Licentia Ltd., Helsinki (FI); Ludwig Institiute for Cancer Research, New York, NY (US)

( * ) Notice: Subject to any disclaimer, the term of this patent is extended or adjusted under 35 U.S.C. 154(b) by 572 days.

(21) Appl. No.: 10/227,081

(22) Filed: Aug. 23, 2002

(65) Prior Publication Data

US 2003/0099687 A1 May 29, 2003

(30) Foreign Application Priority Data

Aug. 24, 2001 (GB) .......................................... 01206090

(51) Int. Cl.$^7$ ........................ A61K 31/497; A61K 9/08; A61K 9/14; A61K 9/20; A61K 9/48
(52) U.S. Cl. .................. 514/252.18; 424/400; 424/439; 424/451; 424/464; 424/489
(58) Field of Search ................................ 424/400, 439, 424/451, 464, 489; 514/252.18

(56) References Cited

FOREIGN PATENT DOCUMENTS

| GB | 2 332 373 | 6/1999 |
|---|---|---|
| WO | 99/03854 | 1/1999 |
| WO | 00/24412 | 5/2000 |

OTHER PUBLICATIONS

Takayuki Asahara et al., "Local Delivery of Vascular Endothelial Growth Factor Accelerates Reendothelialization and Attenuates Intimal Hyperplasia in Balloon–Injured Rat Carotid Artery" Circulation, vol. 91(11), pp. 2793–2801 (1995).

Mikko O. Hiltunen et al., "Intravascular Adenovirus–Mediated VEGF–C Gene Transfer Reduces Neointima Formation in Balloon–Denuded Rabbit Aorta" Circulation, vol. 102, pp. 2262–2268 (2000).

Olli Leppänen et al., "Intimal Hyperplasia Recurs After Removal of PDGF–AB and –BB Inhibition in the Rat Carotid Artery Injury Model" Arterioscler Thromb Vasc Biol., vol. 20, pp. e89–e95 (2000).

M. Myllärniemi, "Selective tyrosine kinase inhibitor for the platelet–derived growth factor receptor in vitro inhibits smooth muscle cell proliferation after reinjury of arterial intima in vivo," Cardiovascular Drugs and Therapy, vol. 13, pp. 159–168 (1999).

*Primary Examiner*—Thurman K. Page
*Assistant Examiner*—Simon J. Oh
(74) *Attorney, Agent, or Firm*—Oona A. Jackson; George R. Dohmann

(57) ABSTRACT

The invention relates to a combination of (a) an inhibitor of platelet-derived growth factor (PDGF) activity and (b) a vector for vascular endothelial growth factor (VEGF-, especially VEGF-C) gene transfer, a pharmaceutical preparation comprising (a) and (b) in combination together with a pharmaceutically acceptable carrier material; a product comprising (a) and (b) as defined above and optionally a pharmaceutically acceptable carrier material, for simultaneous, chronologically staggered or separate use; a method of administering or the use of said combination or product for the treatment of endothelial damage; and/or to the use of (a) and (b) for the manufacture of said pharmaceutical preparation or product for the treatment of endothelial damage.

7 Claims, No Drawings

COMBINATION FOR THE TREATMENT OF ENDOTHELIAL DAMAGE

SUMMARY OF THE INVENTION

The invention relates to a combination of (a) an inhibitor of platelet-derived growth factor (PDGF) activity and (b) a vector for vascular endothelial growth factor (VEGF-, especially VEGF-C) gene transfer, a pharmaceutical preparation comprising (a) and (b) in combination together with a pharmaceutically acceptable carrier material; a product comprising (a) and (b) as defined above and optionally a pharmaceutically acceptable carrier material, for simultaneous, chronologically staggered or separate use; a method of administering or the use of said combination or product for the treatment of endothelial damage; and/or to the use of (a) and (b) for the manufacture of said pharmaceutical preparation or product for the treatment of endothelial damage.

BACKGROUND OF THE INVENTION

Generally, intimal thickening involving inter alia PDGF-triggered smooth muscle cell proliferation and migration is a major complication after surgical, catheter or endoscopic treatment of blood vessels, like treatment of atherosclerosis by angioplasty, stenting or bypass grafting.

For example, restenosis is a frequent complication after percutaneous transluminal coronary angioplasty (PTCA), leading to obstruction in about 20 to 30% of patients within 6 months after the procedure. A key element in the pathogenesis is damage to the endothelium. Dysfunctional or absent endothelium in addition predisposes arteries for various other pathological conditions, inter alia leading to thrombosis and spasm.

Intimal thickening has been described as a response-to-injury phenomenon. Disruption of the protective endothelial cell layer appears to trigger subsequent stimulation of migration and proliferation of smooth muscle cells, partly mediated by PDGF receptor stimulation, which ultimately leads to formation of a neointima composed predominantly of smooth muscle cells and extracellular matrix components. Inhibition of smooth muscle cell proliferation through the use of PDGF antagonists or restoration of the protective endothelial cell layer thus appeared as possible strategies for interference.

Limited beneficial effects have been observed by local treatment with members of the VEGF family, which were demonstrated to increase re-endothelialization and reduce intimal hyperplasia. Similarly, certain effects were observed with various types of PDGF antagonists including PDGF neutralizing antibodies, PDGF receptor antibodies, PDGF aptamers and low-molecular weight tyrosine kinase inhibitors.

For example, gene transfer to the vessel wall was described to provide a new possibility for the treatment of such vascular disorders, especially postangioplasty restenosis. The positive effect of adenovirus-mediated vascular endothelial growth factor (VEGF)-C transfer on neointima formation after endothelial denudation in rabbits has been examined (see M. O. Hiltunen et al., Circulation 102, p. 2262–8 (2000)). Rabbits with balloon-denuded aortas were subjected to gene transfer 3 days after denudation. After 2 and 4 weeks, the intima/media ratio (I/M), histology and cell proliferation were analyzed. 2 weeks after gene transfer, in a control lacZ-transfected control group the I/M ratio was showed a mean value of 0.57, while VEGF-C gene transfer reduced the I/M to a mean value of 0.38 ($p<0.05$ versus lacZ group). Also after 4 weeks, the I/M value for the VEGF-C group was below that for the lacZ-group. It was concluded that VEGF-C gene transfer may be useful for the treatment of postangioplasty restenosis and vessel wall thickening after vascular manipulations. However, the durability of the effect turned out to be questionable (see T. Asahara et al., Circulation 91, 2793–801 (1995) and M. O. Hiltunen et al., Circulation 102, 2262–8 (2000).

On the other hand, a mouse/human chimeric anti-platelet-derived growth factor-β receptor antibody in combination with heparin has been shown to inhibit intimal hyperplasia in the saphenous artery of the baboon after balloon angioplasty (see C. E. Hart et al., Circulation 99, 564–9 (1999)). These data suggested that platelet-derived growth factor plays a key role in the development of intimal lesions at sites of acute vascular injury in the nonhuman primate. Also, the orally active PDGF-receptor tyrosine kinase inhibitor RPR101511A (6,7-di-methoxy-2-thiophen-3-yl-quinoxaline hydrochloride) was shown to inhibit the cell-free and in situ PDGF-receptor tyrosine kinase and PDGF-receptor dependent proliferation and chemotaxis in vascular smooth muscle cells. PTCA in hypercholesterolemic minipigs whose left anterior descending coronary artery had been injured by overdilatation and denudation, yielding a predetermined lesion. In contrast to controls without RPR101511A, the gain in diameter remained in RPR101511A-treated minipigs, and morphometric analysis showed that RPR101511A caused a significant decrease in total intima/media ratio. It was concluded that the PDGF-receptor tyrosine kinase inhibitor RPR101511A prevented angiographic loss of gain following PTCA and significantly reduced histological intimal hyperplasia. In addition, STI571 (N-{5-[4-(4-methyl-piperazino-methyl)-benzoylamido]-2-methylphenyl}-4-(3-pyridyl)-2-pyrimidine-amine as methane sulfonate salt), a low molecular weight inhibitor of PDGF receptor tyrosine kinase, has been described to inhibit smooth muscle proliferation and leasion formation after re-injury of the arterial intima (Myllärniemi et al., Cardiovasc. Drugs and Ther. 13, 159–168 (1999)).

Antagonists of PDGF have, on the other hand, been demonstrated to show beneficial effects in animal restenosis models, but lesion recurrence has been observed after PDGF antagonist withdrawal (see O. Leppänen et al., Arterioscler. Thromb. Vasc. Biol. 20, E89–E95 (2000)).

These findings suggest a need to look for a combination of targeting smooth muscle cells treatment with other strategies.

GENERAL DESCRIPTION OF THE INVENTION

The present invention is based on the surprising finding that smooth muscle cell inhibition (especially with PDGF antagonists) and re-endothelization stimulation (especially with VEGF-C) act together to lead to reduction in intimal hyerplasia ratio paralleled by increased endothelial cell coverage for prolonged times, thus showing that co-treatment with endothelial cell mitogens and inhibitors of smooth muscle cells is a novel principle for vascular injury therapy with prolonged action.

The present invention shows, for the first time, the tying together of the two strategies of causing beneficial effects with PDGF antagonists and increasing of the re-endothelialization with VEGF agonists. In an unprecedented way, the stimulation of one growth factor system, the VEGF system, and the inhibition of a different growth-factor system, the PDGF system, are combined. For the first time, gene therapy and pharmacological treatment are combined successfully.

The nature of endothelial damage is multifactorial, and the treatment schedules suggested so far do not lead to long-lasting positive effects. Under certain circumstances, drugs with different mechanisms of action may be combined. However, just considering any combination of drugs having different mode of action does not necessarily lead to combinations with advantageous effects.

All the more surprising is the experimental finding that in vivo the administration of an inhibitor of platelet-derived growth factor in combination with a vector for vascular endothelial growth factor gene transfer leads to prolonged and significant beneficial effects, e.g. regarding diminished or abolished restenosis.

Not only a beneficial effect, especially a synergistic therapeutic effect, with regard to slowing down, arresting or reversing of endothelial damage, e.g. restenosis, or a longer effect, but also further surprising beneficial effects, e.g. less side-effects, an improved quality of life and a decreased mortality and morbidity, compared to a monotherapy applying only one of the pharmaceutically active ingredients used in the COMBINATION OF THE INVENTION are found.

DETAILED DESCRIPTION OF THE INVENTION

The invention relates to a combination of (a) an inhibitor of platelet-derived growth factor (PDGF) activity and (b) a vector for vascular endothelial growth factor (VEGF-, especially VEGF-C) gene transfer.

In a further aspect, the invention relates to a pharmaceutical preparation comprising (a) and (b) as mentioned in the last paragraph in combination together with a pharmaceutically acceptable carrier material.

The invention also relates to a (commercial) product comprising (a) and (b) as defined above and optionally a pharmaceutically acceptable carrier material, for simultaneous, chronologically staggered or separate use.

The invention also relates to a method of administering, or the use of, said combination of (a) and (b) or said product comprising (a) and (b) for the treatment of endothelial damage, especially for reducing neointima formation and/or restenosis, e.g. after balloon-catheter treatment; and/or to the use of (a) and (b) for the manufacture of a pharmaceutical preparation or said product comprising (a) and (b) for the treatment of endothelial damage, especially as defined above.

Further, the invention relates to component (a), as defined hereinabove or hereinbelow, for use in combination, that is at the same time point or in a chronologically staggered way, with a component (b) as defined hereinabove or hereinbelow, or vice versa a component (b) for use in combination with a component (a) as defined hereinabove or hereinbelow, especially in the treatment of an endothelial damage; especially said components in a packaging and with a description (e.g. package leaflet) suggesting such combination.

The general terms used hereinbefore and hereinafter preferably have within the context of this disclosure the following meanings, unless otherwise indicated:

As components (a) and (b), the following are very preferred:

Component (a): An inhibitor of platelet-derived growth factor (PDGF) activity is preferably a low molecular weight ($M_r$<1500) inhibitor of PDGF-receptor protein-tyrosine kinase, or a pharmaceutically acceptable salt thereof, especially of the 2-phenylaminopyrimidine class, preferably (N-{5-[4-(4-methyl-piperazino-methyl)-benzoylamido]-2-methylphenyl}-4-(3-pyridyl)-2-pyrimidine-amine, especially in the form of the methane sulfonate (monomesylate) salt (STI571), or the 2-thiophen-quinoxaline class, preferably 6,7-dimethoxy-2-thiophen-3-yl-quinoxaline, especially in the form of the hydrochloride salt (RPR101511A).

In the vascular smooth cell proliferation and migration most PDGF effects are mediated by the PDGF-β receptor (activated by PDGF BB, when co-expressed with PDGF-α R, also by PDGF AB), therefore inhibitors active on its kinase are especially preferred.

For a review on PDGF see C.-H. Heldin and B. Westermark, Physiological Reviews 79(4), 1283 (1999).

Combination partner (a) preferably can be prepared and administered as described in WO 99/03854, especially the monomesylate salt of N-{5-[4-(4-methyl-piperazino-methyl)-benzoyl-amido]-2-methylphenyl}-4-(3-pyridyl)-2-pyrimidine-amine can be formulated as described in Examples 4 and 6 of WO 99/03854.

Component (b): A vector for vascular endothelial growth factor (VEGF, VEGF-B, VEGF-D0, especially VEGF-C) gene transfer is especially a vector appropriate for permanent or temporary transfection of mammalian cells, especially a "naked" VEGF-C transgene or preferably a vector in the stricter sense based on an adenovirus (leading to extrachromosomal and thus usually transient expression), retrovirus (leading to integration into the genome and thus especially long-lasting effects), adeno-associated virus, herpes virus, autonomous parvoviruses, lentiviruses (like Semliki Forest Virus) or further on nonviral systems, such as direct injection of naked DNA, e.g. plasmids, liposomes filled with such DNA, (preferably biodegradable) microspheres coated with an expression plasmid or the like, comprising a polynucleotide, especially a VEGF-C polynucleotide, preferably a DNA coding for a VEGF-, especially VEGF-C-, active polypeptid, e.g. a prepro-VEGF-C cDNA.

A VEGF-C polynucleotide of the invention comprises a nucleotide sequence that can be hybridized to a polynucleotide that is complementary to the human VEGF-C cDNA sequence specified in SEQ ID NO: 1 of WO 00/24412 under stringent conditions, e.g. the following: hybridization at 42° C. in 50% formamide, 5×SSC, 20 mM $NaPO_4$, pH 6.8; and washing in 1×SSC at 55° C. for 30 minutes; and wherein the nucleotide sequence encodes a polypeptide that binds and stimulates human VEGF receptor 2 and/or 3. It is to be understood that variation in these exemplary hybridization conditions occurs based on the length an GC nucleotide content of the sequence to be hybridized. Formulae standard in the art are appropriate for determining appropriate hybridization conditions, see Sambrook et al., Molecular Cloning: A Laboratory Manual, $2^{nd}$. ed., Cold Spring Harbor Laboratory Press, 1989, §§ 9.47–9.51. In preferred embodements, the VEGF-C polynucleotide further comprises additional sequences that facilitate the VEGF-C gene therapy. On one embodiment, a vetor is a "naked" VEGF-C transgene (without viral, liposomal or other vector to facilitate transfection) is employed for gene therapy. On this embodiment, the VEGF-C polynucleotide perferably comprises a suitable promoter and/or enhancer sequence (promoters/enhancers are generally e.g. cytomegalovirus promoter/enhancer, Rous sarcoma virus promoter, Tie promoter, or simian virus 40 promoter) for expression in the target mammalian cell, the promoter being operatively linked upstream (i.e., 5') of the VERGF-C coding sequence. The VEGF-C polynucleotide also preferably includes a suitable polyadenylation sequence (e.g. the SV40 or human growth hormone gene polyadenylation sequence) operably linked downstream (i.e., 3') of the VEFG-C coding sequence. The polynucleotide may further comprise sequences the only intented function of which is to facilitate large-scale production of the vector, e.g. in bacteria, such as bacterial origin of replication and a sequence encoding a selectable marker. However, in a preferred embodiment, such extraneous sequences are at least partially cleaved off prior to administration to a mammal, especially, human. It is possible to manufacture and administer such polynucleotides to achieve successful gene therapy usingg procedures that have been described in the literature for other transgenes (see, e.g., Isner et al., Circulation 91, 2687–92 (1995) and Isner et al., Hum. Gene Ther. 7, 989–1011 (1996)). A preferred cDNA encoding VEGF-C is that according to ATCC No. 97231 (see WO 00/24412).

Ther term VEGF-C polynucleotide as defined in the last paragraph is not limited to the full sequence for prepro-VEGF-C or VEGF-C, but also includes variations where one of more, preferably up to 50, more especially 1 to three, nucleotides have been replaced by other nucleotides or where one or more, especially up to 500, more preferably up to 400 nucleotides have been removed or added, as long as the polypeptide resulting from transcription and translation retains anti-VEGF-C biological activity, especially as defined in WO 00/24412.

As vector in the stricter sense, any suitable vector may be used to introduce the VEGF-C transgene into the host.

Preferred are replication-deficient adenovirus (Ad) vectors that can be produced in vitro in specific packaging cells that complement deleted or interrupted adenovirus gene products. Examples are helper virus independent Ad vectors, especially E1-substituted Ad (first generation), such as dLE1-Ad, that can be grown in vitro in specific packaging cells that complement gene products, such as the human embryonic kidney derived (HEK) cell line 293 (trans-complementation by the E1 products possible as these cells constitutively express E1 proteins) or cell line 293N3S, e.g. obtaniable by the Stow method, intracellular homologous recombination between partial viral genomes or plasmid recombination. As the E3 region is dispensable from the Ad genome, first generation Ad vectors carry VEGF, especially VEGF-C coding sequences (preferably VEGF-C cDNA, e.g. comprising the prepro-VEGF-C open reading frame), (including promoters (e.g. the cytomegalovirus promoter), enhancers or other regulatory sequences, or polyadenlyation signal sequences, or any combination thereof, in either the E1 or E3 or both regions. As a possible problem with first generation Ad vectors may be immunogenicity, leading to innate, humoral and/or cellular immune responses. Other vectors may require E1 complementation (e.g. the 911 cell line derived from human embryonic retinoblasts, A549 cells carrying a trimmed E1 fragment (base pairs 505 to 4034 of the Ad5 genome), E2A complementation (e.g. with stably transfected HeLa cells with E2A-complementing properties), E4-complementing cell lines (e.g. E4-complementing cell lines like the Vero derived cell line W162), E1/E2-complementation (e.g. the E1- and E2-complementing cell line AE1-2a (A549-derived) or 293-C2), E2B complementation (various HeLa or 293 derived cell lines), or E1- and E4-complementation (e.g. the cell lines VK2-20 or VK-10-9). Preferred are E1, E3-deleted adenovirus from the genome of the therapeutic adenoviruses.

The vectors can be purified by standard methods, such as pelleting, precipitation with polyethylene glycol, CsCl density-gradient ultracentrifugation, or more modern methods such as anion exchange, size exclusion, hydrophobic interaction or chromatography using metalchelated resins.

In embodiments employing a viral vector, preferred polynucleotides still include a suitable promoter and polyadenylation signal as described above. In addition, then the polynucleotide further includes vector polynucleotide sequences (e.g., adenoviral polynucleotide sequences) operably linked to the sequence encoding a VEGF-C polypeptide. In a preferred embodiment, the vector is an adenovirus vector, more preferably a replication-deficient vector.

Preferred is an adenovirus vector that comprises a promoter, e.g. strong viral promotors or non-viral ones (e.g. from cellular genes for phosphoglycerate kinase, actin, histones), especially the human cytomegalovirus promoter, a VEGF-C cDNA (especially coding for prepro-VEGF-C) and a (especially human growth hormone) polyadenlyation signal ligated into an appropriate vector, especially the pCRII vector (Invitrogen) cloned, especially using homologous recombination, preferably into the E1-deleted region of a E1-E3-deleted adenovirus of serotype 5 (see Bar et al., Gene Ther. 1, 51–8/1994)), the pAdenogal vector (see M. Laitinen et al., Hum. Gene Ther. 9, 1481–6 (1998)), preferably produced in 293 EBNA cells (Invitrogen) and purified by ultracentrifugation. Very preferred is an adenovirus vector as described in WO 00/24412, and/or the VEGF-C sequence given in U.S. Pat. No. 6,221,839 and U.S. Pat. No. 6,245,530.

For recent reviews on possible vector systems for gene therapy, see S. Ylä-Herttuala and J. F. Martin, The Lancet 355, 213–222 (2000) and W.-W. Zhang, Cancer Gene Ther. 6(2), 113–38 (1999), for VEGF-coding sequences see V. Joukov et al., EMBO J. 15(2), 290–8 (1996), especially the (prepro-) VEGF-C coding sequence therein.

Where component (a) and (b) are mentioned, also more than one of each of component (a) and/or component (b) may be present, e.g. more than one PDGF-inhibitor and/or more than one vector for VEGF gene transfer. The components each may be present in free form or in the form of pharmaceutically acceptable salts, e.g. in the case of basic salt-forming groups as acid addition salts, e.g. with organic or inorganic acids, for example chloride or mesylate salts, in case of presence of acidic groups in the form of metal, e.g. alkaline metal, or quarternary ammonium salts, e.g. tert-butylammonium salts, or in case that basic and acidic groups are present in the form of inner or mixed salts, and reference to the components is always intended to mean the components in free and/or in salt form.

A combination which comprises a PDGF-receptor tyrosine kinase inhibitor (a), especially N-{-5-[4-(4-methyl-piperazino-methyl)-benzoylamido]-2-methylphenyl}-4-(3-pyridyl)-2-pyrimidine-amine, and (b) a vector for vascular endothelial growth factor (VEGF, especially VEGF-C) gene transfer in which the active ingredients are present independently of each other in free form or in the form of a pharmaceutically acceptable salt and optionally at least one pharmaceutically acceptable carrier, and are together part of a combination preparation or part of a product with separate preparations (e.g. in the sense of a kit of parts) will be referred to hereinafter as a COMBINATION OF THE INVENTION.

The increase in efficiency of a combination of components (a) and (b) over the single components can be observed using standard procedures.

Especially in Example 2, methods are shown that allow the determination of the prolongation of efficiency of the combination when compared with the duration of action of the isolated components (a) and (b), and other advantages—these methods can also be used for different components (a) and (b) than those given in the Examples. Furthermore, different animals can be used (e.g. pigs, minipigs, baboons, rats) instead of rabbits. For example, the intima/media ratio determination allows for judgment of vessel diameter maintenance, while determination of CD31-positive cells allows for the judgment of endothelium cell coverage (in both cases, the higher the measured ratio/% coverage, the better the treatment result).

A pharmaceutical preparation comprising (a) and (b) in combination together with a pharmaceutically acceptable carrier material is a pharmaceutical composition allowing that the combination partners (a) and (b) can be administered together (at the same time) in one combined unit dosage form; or in two separate dosage forms allowing to dose independently or by use of different fixed combinations with distinguished amounts of the combination partners (components) (a) and (b), i.e., simultaneously or at different time points. The unit dosage form may also be a fixed combination of components (a) and (b), which is especially preferred as pharmaceutical preparation comprising (a) and (b) in combination.

The pharmaceutical compositions for separate administration of the combination partners (a) and (b) and for the administration in a fixed combination, i.e. single galenical compositions comprising at least two combination partners (a) and (b), according to the invention can be prepared in a manner known per se and are those suitable for enteral, such as oral or rectal, and parenteral administration to mammals (warm-blooded animals), including humans, comprising a therapeutically effective amount of at least one pharmacologically active combination partner alone or in combination with one or more pharmaceutically acceptable carriers, especially suitable for enteral or parenteral application.

Preferred pharmaceutical preparations are those that comprise any one or both of the components (a) and (b) plus a carrier material (e.g. disintegrants, fillers, preservatives, solvents or the like) and especially provide component (a) and component (b) in a dose that is jointly active to reduce the pathological consequences of damage to vessel endothelium.

Pharmaceutical compositions according to the invention comprise, for example, from about 0.00001 to about 100% of either or both of the active ingredients, preferably in the case of component (a) from about 20% to about 60%, in the case of component (b) from about 0.0001 to about 50%. Pharmaceutical preparations for the combination therapy for enteral or parenteral administration are, for example, those in unit dosage forms, such as sugar-coated tablets, tablets, capsules or suppositories, or ampoules, infusion bags or bottles or the like for liquid preparations. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

Preferably, components (a) and (b) are formulated separately, especially for use in the method of administration according to the invention, component (a) more preferably for parenteral (e.g. infusion or injection) or more preferably enteral use, e.g. as a capsule or tablet or drink, component (b) more preferably as a solution or suspension in a sterile aqueous solution that may comprise additional salts, polysaccharides, sugars, like glucose, like dextrose, or buffers, e.g. phosphate-buffered saline, especially in physiological saline (0.9% NaCl), or as dry form allowing completion prior to use by addition of water or an aqueous solution with buffers, salts or polysaccharides, or the like, e.g. physiological saline.

In particular, a therapeutically effective amount of each of the combination partners of the COMBINATION OF THE INVENTION may be administered simultaneously or sequentially and in any order, and the components may be administered separately or as a fixed combination. For example, the method of delay of progression or treatment of a proliferative disease and/or acute or chronic transplant rejection according to the invention may comprise (i) administration of the combination partner (a) in free or pharmaceutically acceptable salt form and (ii) adminstration of a combination partner (b) in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners of the COMBINATION OF THE INVENTION can be administered separately at different times during the course of therapy or concurrently in divided or single combination forms. Furthermore, the term "administering" also encompasses the use of a pro-drug of a combination partner that converts in vivo to the combination partner as such. The instant invention is therefore to be understood as embracing all such regimes of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, the severity of the condition being treated. Thus, the dosage regimen for the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

Component (a), especially N-{5-[4-(4-methyl-piperazino-methyl)-benzoylamido]-2-methylphenyl}-4-(3-pyridyl)-2-pyrimidine-amine monomesylate, is preferably administered to a human in a dosage in the range of about 2.5 to 2000 mg/day, more preferably 5 to 600 mg/day and most preferably 20 to 300 mg/day. Unless stated otherwise herein, the compound is preferably administered from one to four times per day.

Component (b) is preferably used in a dosage that corresponds to $1 \times 10^7$ to $1 \times 10^{11}$ pfu/ml, preferably a total of 0.1 to 20 ml, more preferably 1 to 10 ml being administered.

Administration of component (b) is preferably effected by local drug delivery, especially employing a local drug delivery catheter (e.g. from Boston Scientific; see Camendzind et al., Circulation 92, 2463–72, 1995). Thus, the corresponding formulation may be a solution in an aqueous medium appropriate for injection or infusion, or the dry form (e.g. lyophilisate) to be completed with an aqueous medium, e.g. a buffer solution in water, physiological saline or dextrose solution of osmotically appropriate composition. For preferred administration variants, see WO 00/24412, e.g. local administration or administration before, during or after vascular surgery or catheter treatment.

A product comprising (a) and (b) as defined above and optionally a pharmaceutically acceptable carrier material, for simultaneous, chronologically staggered or separate use, is preferably a commercial package or kit of parts comprising a pharmaceutical formulation of component (a) and one of component (b), respectively, that are labeled for combined or chronologically staggered or (in a broader, less preferred aspect) separate use.

The term "a (commercial) product comprising (a) and (b)", as used herein defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger (especially longer-lasting) than the effect which would be obtained by use of only any one of the combination partners (a) and (b) alone or after long time intervals not allowing mutual influence. The ratio of the total amounts of the combination partner (a) to the combination partner (b) to be administered in the combined preparation can be varied, e.g. in order to cope with the needs of a patient subpopulation to be treated or the needs of the single patient which different needs can be due to the particular disease, age, sex, body weight, etc. of the patients. Preferably, the combination leads to a joint therapeutic effect not observable with single administration or separate administration after long time intervals, thus corresponding to independent administration; especially, there is at least one beneficial effect, e.g., a mutual enhancing of the effect of the combination partners (a) and (b), in particular a synergism, e.g. a more than additive effect, additional advantageous effects, less side effects, a combined therapeutical effect in a non-effective dosage of one or both of the combination partners (a) and (b), and very preferably a strong synergism of the combination partners (a) and (b). Especially preferred is prolonged action against restenosis.

Moreover, the present invention provides a commercial package comprising as active ingredients a COMBINATION OF THE INVENTION, together with instructions for simultaneous, separate or sequential use thereof in the delay of progression or treatment of an endothelial damage.

Endothelial damage is especially surgically or catheter/endoscopically induced endothelial damage, preferably pathological neointima formation, restenosis and/or vein graft thickening, e.g. after balloon-catheter treatment, surgical carotid artery endarterectomy, stent implantation, angioplasty (e.g. balloon catheter dilatation of arteries, e.g. the aorta, a femoral artery, a carotid artery or a coronary artery, balloon-induced arterial injury) or bypass graft.

The use of/method of administering a COMBINATION OF THE INVENTION, especially said combination or product for the treatment of endothelial damage preferably aims at diminishing or abolishing said endothelial damage, e.g. by maintaining the diameter gain of a vessel after dilatation or surgery, palliatively or even practically perpetually.

Preferably, component (a) is administered enterally, e.g. p.o. (orally), while component (b), at the same time, before (especially shortly before, e.g. within 24 h or less) or after (especially shortly after, e.g. within 24 h or less) (so as to allow an effect superior to that of administration of the single components only, especially one as described to allow a joint therapeutic effect not observable with single administration or separate administration after long time intervals), is administered enterally, preferably as described above; in both cases preferably to a mammal, especially a human, requiring such treatment and preferably in a dose that allows for the treatment of endothelial damage, especially of the types described above.

Finally, the invention relates also to the use of components (a) and (b) for the manufacture of a COMBINATION OF THE INVENTION, especially a combination or product as described above and below, for the treatment of endothelial damage (especially as defined above).

Where references are mentioned throughout this disclosure, they are incorporated by references herewith, especially with regard to those passages therein that are relevant at the places of quotation within this text.

PREFERRED EMBODIMENTS OF THE INVENTION

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred; in each case, the definitions described hereinbefore as being preferred or exemplary are preferred.

(1) The invention relates especially to a combination of (a) an inhibitor of platelet-derived growth factor activity and (b) a vector for vascular endothelial growth factor gene transfer, where the components (a) and (b) may be separate or in fixed combination.

(2) Preferred is a combination according to the last paragraph, wherein the inhibitor of platelet-derived growth factor activity (a) is a low molecular weight ($M_r$<1500) inhibitor of PDGF-receptor protein-tyrosine kinase, or a pharmaceutically acceptable salt thereof, especially of the 2-phenylaminopyrimidine class, preferably (N-{5-[4-(4-methyl-piperazino-methyl)-benzoylamido]-2-methylphenyl}-4-(3-pyridyl)-2-pyrimidine-amine, especially in the form of the methane sulfonate salt, or of the 2-thiophen-quinoxaline class, preferably 6,7-dimethoxy-2-thiophen-3-yl-quinoxaline, especially in the form of the hydrochloride salt, and the vector for vascular endothelial growth factor gene transfer (b) is especially a vector appropriate for permanent or temporary transfection of mammalian cells, especially a vector based on an adenovirus, retrovirus, adeno-associated virus, herpes virus, autonomous parvoviruses, lentiviruses or further on nonviral systems selected from naked DNA, liposomes filled with such DNA, microspheres coated with an expression plasmid or the like, comprising a DNA coding for VEGF- especially VEGF-C, e.g. a prepro-VEGF-C cDNA; more preferably an adenovirus vector that comprises a promoter, a VEGF-C cDNA (especially coding for prepro-VEGF-C) and a polyadenlyation signal ligated into a pCRII vector cloned into the E1-deleted region of a E1-E3-deleted adenovirus of serotype 5.

(3) A preferred aspect of the invention also relates to a pharmaceutical preparation comprising components (a) and (b) as defined in the last two paragraphs in combination together with a pharmaceutically acceptable carrier material.

(4) A further preferred aspect of the invention relates to a product comprising components (a) and (b) as defined in paragraphs (1) or (2) above and optionally a pharmaceutically acceptable carrier material, for simultaneous, chronologically staggered or separate use, especially in the treatment of endothelial damage. Preferred is such a product wherein components (a) and (b) are formulated separately, especially for use in the method of administration according to the invention, component (a) for parenteral or more preferably enteral use together with a pharmaceutically acceptable carrier material, especially as a capsule or tablet or drink, component (b) as a solution or suspension in a sterile aqueous solution that may comprise additional salts, polysaccharides, like dextrose, or buffers, especially in physiological saline (0.9% NaCl), or as dry form allowing completion prior to use by addition of water or an aqueous solution with buffers, salts or polysaccharides, or the like, e.g. physiological saline.

(5) Very preferred is a product according to the last paragraph, where the endothelial damage is surgically or catheter/endoscopically induced endothelial damage, preferably pathological neointima formation, restenosis and/or vein graft thickening, more especially after balloon-catheter treatment, surgical carotid artery endarterectomy, stent implantation, angioplasty or bypass graft.

(6) The invention preferably also relates to a method of treating a warm-blooded animal having an endothelial damage comprising administering to the animal a combination which comprises component (a) and component (b) according to any one of paragraphs (1) and (2) above in a quantity which is jointly therapeutically effective against an endothelial damage and in which the components can also be present in the form of their pharmaceutically acceptable salts.

(7) Especially preferred is a method of administering or the use of a combination according to any one of paragraphs (1) and (2) above, where components (a) and (b) may be administered together or in chronologically staggered manner, or preferably of a product according to any one of paragraphs (4) and (5) above for the treatment of endothelial damage, especially surgically or catheter/endoscopically induced endothelial damage, preferably pathological neointima formation, restenosis and/or vein graft thickening, more especially after balloon-catheter treatment, surgical carotid artery endarterectomy, stent implantation, angioplasty or bypass graft.

(8) A preferred aspect of the invention also relates to the use of components (a) and (b) as defined in paragraph (1) or (2) above for the manufacture of a pharmaceutical preparation according to paragraph (3) above or a product according to any one of paragraphs (4) and (5) above for the treatment of endothelial damage, especially where the endothelial damage is surgically or catheter/endoscopically induced endothelial damage, preferably pathological neointima formation, restenosis and/or vein graft thickening, more especially after balloon-catheter treatment, surgical carotid artery endarterectomy, stent implantation, angioplasty or bypass graft.

Very preferred aspects of the present invention (especially components (a), (b), their way of administration, and pharmaceutical preparations therewith) are embodied by the subsequent examples:

EXAMPLES

The following examples illustrate the invention without limiting the scope thereof.

Example 1

Adenovirus Constructs

Adenovirus containing the complete prepro-VEGF-C open reading frame operably linked to a cytomegalovirus (CMV) promoter and human growth hormone polyadenylation signal is conctructed as follows: A DNA comprising a CMV promotor sequence is prepared by digesting the pcDNA3.1+ vector (Invitrogen) with Sal I and filling the 5'-overhangs with the Klenow enzyme. The CMV promoter (nucleotides 5431–911) is excised from the vector with Hind III and isolated. A full-length human VEGF-C cDNA containing the 1997-bp sequence specified in SEQ ID NO: 1 in WO 00/24412 (as well as less than 50 bases of additional non-coding and polylinker sequences) is excised from a previously constructed VEGF-C pREP7 expression vector (see WO 98/33917) with Hind III and Xho I and isolated. A human growth hormone polyadenylation signal (about 860 bp) is excised from an αMHC with SalI and BamHI. The CMV promoter, VEGF-C cDNA, and the hGH polyadenylation signal fragments are simultaneously ligated into a BamHI and EcoRV digested pCRII vector (for the ligated CMV promoter and VEGF-C cDNA see WO 00/24412, SEQ ID NO: 17). The resulting construct is opened with BglII and partially digested with BamHI. The full transcriptional unit is ligated into BglII-opened pAdBglII vector. This construct (designated pAdBglII VEGF-C) is then used to create recombinant adenovirus containing the CMV-VEGF-C-hGH transcriptional unit, using standard homologous recombination techniques (Barr et al., Gene Ther. 1, 51–58 (1994)). Replication-deficient E1-E3 deleted adenoviruses are produced in 293 cells and concentrated by ultracentrifugation using techniques known in the literature (see, e.g., Barr et al., 1994, lic. cit.). A control plasmid comprising the lacZ gene operably linked to the same promoter is also used (see Laitinen, M., et al., Hum. Gene Ther. 9, 1481–6 (1998)). The lacZ adenovirus has a nuclear targeted signal in order to direct the β-galactosidase expression to the nucleus. Replication deficient E1-E3 deleted adenoviruses are produced in 293 cells and concentrated by ultracentrifugation (see Barr et al., 1994, loc. cit.). The adenoviral preparations are analyzed for the absence of helper viruses, lipopolysaccharide and bacterial contaminants (see Laitinen et al., Hum. Gene Ther. 9, 1481–6 (1998) and Puumalainen et al., Hum. Gene Ther. 9, 1769–74 (1998)).

Example 2

Evaluation of the Effects of Combining PDGF Antagonists with VEGF-C Gene Transfer A rabbit model of restenosis is used. In this model, rabbits are put on a cholesterol-enriched diet and subjected to balloon catheter injury two weeks later.

Animals are randomized into four treatment groups which are analyzed at two different time-points after balloon injury. The control group is subjected to local LacZ adenovirus gene transfer three days after denudation, one of the single treatment groups is given VEGF-C adenovirus together with sterile water, the other receives LacZ gene transfer with three weeks of treatment with systemic (enteral) administration of the PDGF-receptor antagonist STI571. Finally, one group receives both VEGF-C gene transfer and STI571. One set of animals is analyzed three weeks after start of the therapy, the other is analyzed six weeks after start of the therapy, i.e. three weeks after the last oral drug administration.

In detail, a 2 cm long de-endothelialized aortic segment is subjected to local intravascular VEGF-C or LacZ (control) gene transfer. After gene transfer with VEGF-C or LacZ viruses, animals receive a 3-week systemic course with STI571 or carrier. Intima to media ration (mean±SEM) is determined at the discontinuation of the systemic therapy (3-week end-point) or after an additional 3-week period without treatment (6-week endpoint). The extent of intimal hyperplasia, after the four different treatments, is quantified by planimetry (Table 1). At the three-week endpoint, the two groups subjected to VEGF-C gene transfer demonstrate a reduction in lesion formation with intima:media ratios of 0.23±0.02 and 0.24±0.05 as compared to the control treated animals (0.38±0.05). The effect is completely due to a decrease in lesion size and does not involve vascular remodeling (as demonstrable by equal lengths of external (EEL) and internal elastic lamina (IEL) in all study groups (data not shown).

Consistent with a more pronounced lesion, the intima:media ratio in the control group is increased to 0.51±0.08 at six weeks (Table 1). Therapy with VEGF-C gene transfer alone fails to show the beneficial effect observed at an earlier time point, in line with previous observations of only a transitory effect without durability. Interestingly, however, when the animals receive both VEGF-C and STI571, a significant reduction of intima:media ratio to 0.23±0.05 is obtained.

Animals from the 8 groups are also analyzed with regard to luminal endothelial cell coverage from transverse vessel sections. This variable is determined by analysis of the percentage of the luminal surface that is covered by CD31-positive cells (CD31 is an endothelium-specific antibody from DAKO).

TABLE 1

Intima:media ratios and CD31 positive cell coverage

| group | intima:media ratio | | | CD31 positive cell coverage (% of luminal circumference) | | |
|---|---|---|---|---|---|---|
| | n | mean | SEM | n | mean | SEM |
| a) 3-week endpoint: | | | | | | |
| H$_2$O + LacZ | 5 | 0.38 | 0.05 | 5 | 38.7 | 9.9 |
| H$_2$O + VEGF-C | 6 | 0.23* | 0.02 | 6 | 37.5 | 9.4 |
| STI571 + LacZ | 5 | 0.33 | 0.06 | 5 | 33.7 | 9.8 |
| STI571 + VEGF-C | 5 | 0.24* | 0.05 | 5 | 58.1 | 7.6 |
| b) 6-week endpoint | | | | | | |
| H$_2$O + LacZ | 5 | 0.51 | 0.08 | 5 | 39.3 | 12.9 |
| H$_2$O + VEGF-C | 5 | 0.38 | 0.07 | 5 | 73.7* | 11.0 |
| STI571 + LacZ | 6 | 0.50 | 0.12 | 6 | 60.2 | 7.0 |
| STI571 + VEGF-C | 5 | 0.23* | 0.05 | 5 | 72.1* | 7.3 |

*= significant vs. H$_2$O + LacZ by ANOVA

To investigate the mechanism underlying the observed beneficial effect of the combination therapy, the extent of endothelialization and the number of smooth muscle cells at the transfected vessel segment are analyzed (see Table 1). At the three-week time point, no difference in endothelial cell coverage is observed between the groups, although a trend towards an increased endothelial cell coverage in the combination group is seen (P=0.088). However, at the six-week time point, both groups that have received VEGF-C gene transfer display an increase in endotheilialization as compared to the control group. The addition of STI571 treatment does not lead to additional stimulatory effects on re-endothelialization. The fraction of proliferating intimal smooth muscle cells, measured by BrdU labelling of dividing cells at the end of the study period, is similar between the groups, and thus does not indicate a risk for lesion recurrence. As shown in Table 4 (see below), the cell number is reduced by 52% (P<0.05) in the combination group as compared to control animal.

The cohort groups are also characterized with regard to animal weights, weight changes, extent of balloon injury (IEL damage), blood lipid profiles and basic hematologic parameters. No differences between the groups are observed (see Table 2 below). Further, no signs of toxicity to internal organs, inflammation or foam cell accumulation at the site of gene transfer were detected as judged by histology and immunostainings (not shown).

In order to exclude influence of PDGF inhibition on vector uptake or transgene expression, the LacZ expression is compared between the groups that have received either STI571 or carrier (see Table 4 below). The effect of VEGF-C therapy on blood STI571 levels is, in addition, measured in animals that have received LacZ or VEGF-C adenovirus.

Experimental Details a) Denudation and Gene Transfer

42 New Zealand White rabbits (National Laboratory Animal Center, Kuopio, Finland) weighing 2.3 to 2.8 kg are randomized into 8 experimental groups (n=5 or 6). All animal experimentations are performed at the National Laboratory Animal Centre, Kuopio, Finland, and the study protocol is approved by the local Ethics Committee. Cholesterol-feeding, aortic injury and subsequent gene transfer basically takes place as described in Hiltunen et al., Circulation 102, 2262–8 (2000). Briefly, a 0.25% cholesterol diet is begun two weeks before the denudation injury of the aorta and is continued thoughout the experiment. Denudation is achieved by repeated passage of a 4 F arterial embolectomy catheter (Sorin Biomedicl). Three days later, intravascular gene transfer is performed with a local drug delivery catheter (Boston Scientific; see Camendzind et al., Circulation 92, 2463–72, 1995). A virus titer of $1.15 \times 10^{10}$ pfu is used in the final volume of 10 ml in 0.9% sterile saline, and the catheter is inflated to 6 atm pressure and the solution infused for 10 minutes (1.0 ml/min) to a 2 cm long infrarenal abdominal aortic segment free of side branches. The intravascular procedures are performed under full surgical anesthesia with Fluanisone/Fentanyl (Fluanisone®=1-(4-fluorophenyl)-[4-(2-methoxyphenyl)-1-piperazinyl]-1-butanone: 10 mg/ml, Fentanyl®=N-phenyl-N-[1-(2-phenylethyl)-4-piperidinyl]-propanamide: 0.2 mg/ml; Hypnorm vet®, Janssen Pharmaceuticals), the animals are premedicated with 1.25 mg/kg body weight midazolam (5 mg/ml, Dormicum, Roche), and receive 125 mg preoperative metronidazole (Zinacef, Glaxo Wellcome) and are heparinized (1000 IU) before catheterization. At the end of follow-up full surgical anesthesia is again induced as above and the animals are euthanized with an overdose.

b) Administration of STI571:

STI571 is dissolved in sterile water (2 mg/ml) shortly before administration and given with a dosage of 10 mg×kg$^{-1}$×d$^{-1}$, divided into to daily doses. The drug, or control (=sterile water) is administered with an oro-gastric sond on trained, unsedated animals 1 h before the gene transfer and is repeated every 12 h thereafter for the following three weeks.

c) Sampling for Blood for Determination of STI571

Blood sampling, not commencing with catheterizations or euthanasia, is performed under slight Fluanisone/Fentanyl sedation. Samples for STI571 level determination are obtained 2 h after drug delivery and immediately before the next scheduled administration at the 3$^{rd}$ and 10$^{th}$ days after gene transfer, and at the day of euthanasia (21 or 42 days after gene transfer). The specimen is stored in heparinized tubes shielded from light and plasma is isolated by centrifugation within 2 h and stored at −70° C. STI concentration is determined by high-performance liquid chromatography For HPLC, plasma proteins are precipitated by the addition of an equal volume of acetonitrile. After 20 to 30 min at room temperature, the precipitated proteins are removed by centrifugation (10,000 g, 5 min) and the supernatants are analyzed by reversed-phase HPLC.

HPLC is performed on Merck-Hitachi LaChrom® equipment. 100 μl of the supernatants are injected onto a Nucleosil® 100-5 C18 column (C-18 modified silica Gel, Macherey & Nagel) protected by a 20 mm guard column of the same material. The sample is eluted with a gradient of acetonitrile in water at a flow rate of 1 ml/min; after 5 min at 10% v/v acetonitrile, the concentration of acetonitrile is increased to 75% v/v over a period of 15 min. The column is prepared for the next sample by washing for 5 min with 75% v/v acetonitrile, returning to 10% acetonitrile over 5 min and 5 min reequilibration. The mobile phase contains 0.05% v/v trifluoroacetic acid. The eluent is monitored using UV absorbance at a wavelength of 265 nm. The compound is found to elute with a retention time of about 13.2 min. The concentration of the compound is determined by the external standard method using peak heights. A calibration curve is constructed by adding known amounts of STI571 to plasma or tumor homogenates from untreated animals. The calibration standards are processed as above. Calibration curves are fittted by linear regression analysis and are found to be linear over the whole range measured (0.047–23.65 μg free base per ml).

Results:

TABLE 2

Determination of plasma STI571 concentration:

| Plasma STI571 concentration | day 3 | | day 10 | | day 21 | | |
|---|---|---|---|---|---|---|---|
| (μM) | peak | nadir | peak | nadir | peak | nadir | day 42 |
| LacZ transfected animals | 10.27 ± 1.28 | 3.57 ± 0.74 | 16.63 ± 1.99 | 5.16 ± 1.89 | 13.18 ± 1.65 | 3.86 ± 1.02 | 0.04 ± 0.01 |
| VEGF-C transfected animals | 11.08 ± 1.10 | 3.11 ± 1.13 | 14.26 ± 1.26 | 2.41 ± 0.43 | 13.58 ± 1.95 | 2.95 ± 0.90 | 0.05 ± 0.01 | d) Diagnostic Autopsy and Hematology, Serum Lipid Profile 24 animals (n=3/group) are subjected to diagnostic autopsy (Dr. P. Syrjälä, National Veterinary and Food Research Institute, Kuopio, Finland) immediately after removal of the transferred vessel segment. Samples from multiple organs (liver, kidney, lung, spleen, heart, adrenal gland, thyroid, testis, epididymis, bone marrow, jejunum, gastric ventricle, pancreas and cerebrum) are processed for hematoxylin-eosin staining and subsequently analyzed with microscopy. Blood samples are drawn for complete blood count at the time of euthanasia from randomly selected animals (n=3/group) in the 3-week endpoint cohort.

For determination of lipid profile, samples are taken at the time of endothelial denudation, at 16 days after gene transfer and at euthanasia Results:

TABLE 3

Quantification of vessel wall injury, animal weights, hematological parameters and serum lipid profiles

| | 3-week endpoint | | | |
|---|---|---|---|---|
| VEGF-C/ STI571 | −/− | +/− | −/+ | +/+ |
| IEL damage (%) | 23.6 ± 2.4 | 29.3 ± 1.1 | 27.6 ± 2.6 | 24.0 ± 2.0 |
| weight (g) | 2551 ± 90 | 2624 ± 150 | 2618 ± 124 | 2625 ± 66 |
| CBC[1] | | | | |
| Hct (%) | 32 ± 2.7 | 33 ± 1.4 | 31 ± 1.2 | 33 ± 1.3 |
| Hb (g/l) | 109 ± 6.4 | 111 ± 4.9 | 103 ± 3.6 | 105 ± 4.6 |
| MCH (pg) | 23 ± 0.3 | 23 ± 0.3 | 21 ± 0.8 | 21 ± 1.0 |
| MCV (fl) | 67 ± 1.2 | 66 ± 0.3 | 64 ± 2.0 | 66 ± 1.4 |
| MCHC (g/l) | 341 ± 8.6 | 339 ± 4.6 | 335 ± 4.7q | 321 ± 8.5 |
| RBC count (× 10$^{12}$/l) | 4.8 ± 0.3 | 4.9 ± 0.2 | 4.9 ± 0.2 | 5.0 ± 0.3 |
| WBC count (× 10$^{9}$/l) | 5.4 × 0.2 | 5.3 × 2.0 | 4.6 ± 0.6 | 4.7 ± 0.4 |
| Bands (%) | 0 ± 0 | 0 ± 0 | 0 ± 0 | 0 ± 0 |
| neutrophils (%) | 19.0 ± 4.0 | 26.7 ± 3.2 | 26.8 ± 2.7 | 27.3 ± 2.7 |
| lymphocytes (%) | 77.7 ± 5.8 | 71.0 ± 3.5 | 67.4 ± 4.1 | 65.0 ± 3.8 |

TABLE 3-continued

Quantification of vessel wall injury, animal weights, hematological parameters and serum lipid profiles

| | | | | |
|---|---|---|---|---|
| monocytes (%) | 1.3 ± 0.7 | 1.3 ± 0.8 | 2.4 ± 0.7 | 2.7 ± 0.3 |
| eosinophiles (%) | 2.0 ± 1.5 | 1.0 ± 0.6 | 3.4 ± 1.4 | 5.0 ± 1.5 |
| basophiles (%) | 0 ± 0 | 0 ± 0 | 0 ± 0 | 0 ± 0 |
| Lipids (mM) | | | | |
| S-Chol | 10.2 ± 3.4 | 13.5 ± 2.3 | 11.7 ± 2.4 | 13.0 ± 2.6 |
| HDL | 0.512 ± 0.08 | 0.50 ± 0.08 | 0.69 ± 0.11 | 0.42 ± 0.07 |
| LDL | 9.3 ± 3.3 | 12.2 ± 2.3 | 10.2 ± 2.3 | 11.9 ± 2.3 |
| S-TG | 1.0 ± 0.1 | 1.9 ± 0.5 | 1.8 ± 0.3 | 1.5 ± 0.7 |

6-week end point

| | | | | |
|---|---|---|---|---|
| no. of animals | 5 | 5 | 6 | 5 |
| IEL damage (%) | 23.9 ± 2.6 | 23.1 ± 2.1 | 21.8 ± 1.5 | 29.2 ± 6.5 |
| weight (g) | 2596 ± 160 | 2716 ± 155 | 2462 ± 90 | 2623 ± 160 |
| Lipids (mM) | | | | |
| S-Chol | 14.9 ± 2.1 | 14.6 ± 2.0 | 16.5 ± 3.5 | 14.6 ± 2.8 |
| HDL | 0.52 ± 0.04 | 0.57 ± 0.09 | 0.53 ± 0.05 | 0.52 ± 0.02 |
| LDL | 13.4 ± 2.0 | 12.8 ± 1.8 | 14.5 ± 3.2 | 11.8 ± 2.5 |
| S-TG | 2.1 ± 0.1 | 2.6 ± 0.6 | 3.3 ± 0.6 | 4.9 ± 1.1 |

The following abbreviations are used:
IEL: Internal elastic lamina;
CBC: complete blood count;
Hct: hematocrit;
Hb: hemoglobin;
MCH: mean corpuscular hemoglobin;
MCV: mean red cell volume;
MCHC: mean corpuscular hemoglobin concentration;
RBC: red blood cell;
WBC: white blood cell;
S-Col: serum-cholesterol;
HDL: high-density lipoprotein;
LDL: low-density lipoprotein;
S-TG: serum triglyceride.
[1] Cell counting is performed on a bloodsmear preparation. No data on platelet count available.
Data are shown as mean ± SEM.

e) Histopathology and Immunostaining

Three hours before euthanasia, animals receive an i.v. injection of 50 mg 5-bromo-2'-deoxyuridine (BrdU; Zymed Laboratories, San Francisco, Calif., USA) dissolved in 40% ethanol. After euthanasia, the transferred vessel segment is removed, flushed gently with saline, and divided into 4 parts of equal length. The proximal part is snap-frozen in liquid nitrogen and stored at −70° C. The next part is immersion-fixed in 4% paraformaldehyde/15% sucrose (pH 7.4) for 4 h, rinsed in 15% sucrose (pH 7.4) and embedded in paraffin. The $2^{nd}$ most distal part is fixed in 70% ethanol overnight and embedded in paraffin. The distal part is fixed in 4 5 paraformaldehyde/PBS (pH 7.4) for 10 minutes, rinsed in PBS, embedded in OCT compound (Miles) and stored at −70° C. The distal segments from 3 week end-point animals are stained for β-galactosidase activity in X-Gal staining solution at +37° C. for 16 h, followed by fixation similar to that for the second segment. Paraffin sections are used for the detection of endothelium (CD31, DAKO, 1:50), smooth muscle cells (HHF, DAKO, 1:50), macrophages (RAM-11, DAKO, 1:50), and BrdU positive cells (Bu20a, DAKO, 1:50). Controls for immunostainings include incubations with class- and species-matched immunoglobulins and omission of primary antibodies. Morphometry is performed with Leica Q50011W software with a stereomicroscope connected to a digital camera (Leica). All measurements are performed by an individual blinded to treatment allocation, and two observers control the measurements from randomly selected multiple samples without knowledge of the origin of the sections.

TABLE 4

Quantification of the intimal and medial cell number and of fraction of BrdU positive Smooth Muscle Cells (SMC)

| | 6-week endpoint | | | |
|---|---|---|---|---|
| VEGF-C/ STI571 | −/− | +/− | −/+ | +/+ |
| BrdU positive SMC (%) | | | | |
| intima | 0.62 ± 13.13 | 0.35 ± 0.11 | 0.57 ± 0.13 | 0.44 ± 0.17 |
| media | 0.35 ± 0.08 | 0.24 ± 0.08 | 0.39 ± 0.08 | 0.38 ± 0.15 |
| Number of SMC | | | | |
| intima | 1540 ± 212 | 1344 ± 296 | 1471 ± 287 | 747 ± 158 |
| media | 2690 ± 216 | 2537 ± 132 | 2403 ± 381 | 2117 ± 188 | f) Statistical Analysis

StatView 5.0 software (Abacus Concepts) is used for all statistical calculations. All values are expressed as mean±SEM. Means are compared by ANOVA, or unpaired t-test where appropriate. Statistical significance is accepted at the 95% confidence level.

What is claimed is:

1. A combination of (a) an inhibitor of platelet-derived growth factor activity, which is selected from N-(5-[4-(4-methyl-piperazino-methyl)-benzoylamido]-2-methylphenyl)-4-(3-pyridyl)-2-pyrimidine-amine and/or 6,7-dimethoxy-2-thiophen-3-yl-quinoxaline, or a pharmaceutically acceptable salt thereof, and (b) a vector appropriate for gene transfer comprising a vascular endothelial growth factor gene, where the components (a) and (b) may be separate or in fixed combination.

2. A pharmaceutical preparation comprising components (a) and (b) as defined in claim 1 in combination together with a pharmaceutically acceptable carrier material.

3. A product comprising components (a) and (b) as defined in claim 1 and optionally a pharmaceutically acceptable carrier material, for simultaneous, chronologically staggered or separate use, especially in the treatment of endothelial damage.

4. A product according to claim 3, wherein components (a) and (b) are formulated separately, especially for use in the method of administration according to the invention, component (a) for parenteral or more preferably enteral use together with a pharmaceutically acceptable carrier material, especially as a capsule or tablet or drink, component (b) as a solution or suspension in a sterile aqueous solution that may comprise additional salts, polysaccharides, like dextrose, or buffers, especially in physiological saline (0.9% NaCl), or as dry form allowing completion prior to use by addition of water or an aqueous solution with buffers, salts or polysaccharides, or the like, such as physiological saline.

5. A product according to claim 3 where the endothelial damage is surgically or catheter/endoscopically induced endothelial damage, preferably pathological neointima formation, restenosis and/or vein graft thickening, more especially after balloon-catheter treatment, surgical carotid artery endarterectomy, stent implantation, angioplasty or bypass graft.

6. A method of treating a warm-blooded animal having an endothelial damage comprising administering to the animal a combination which comprises component (a) and component (b) according to claim 1 in a quantity which is jointly therapeutically effective against an endothelial damage and in which the components can also be present in the form of their pharmaceutically acceptable salts.

7. A method of administering a combination according to claim 1, where components (a) and (b) may be administered together or in chronologically staggered manner for the treatment of endothelial damage, especially surgically or catheter/endoscopically induced endothelial damage, preferably pathological neointima formation, restenosis and/or vein graft thickening, more especially after balloon-catheter treatment, surgical carotid artery endarterectomy, stent implantation, angioplasty or bypass graft.

* * * * *